United States Patent [19]
Hauck

[11] 3,943,149
[45] Mar. 9, 1976

[54] NAPHTHYLOXY ACETIC ACIDS AND RELATED COMPOUNDS
[75] Inventor: Frederic Peter Hauck, Somerville, N.J.
[73] Assignee: E. R. Squibb & Sons, Inc., Princeton, N.J.
[22] Filed: Apr. 3, 1975
[21] Appl. No.: 564,928

Related U.S. Application Data
[62] Division of Ser. No. 305,619, Nov. 10, 1972, Pat. No. 3,906,032.

[52] U.S. Cl. .............................................. 260/340.5
[51] Int. Cl.² ........................................ C07D 317/08
[58] Field of Search ................................ 260/340.5

[56]         References Cited
         UNITED STATES PATENTS
3,538,227  11/1970  Bencze .......................... 260/520 X
3,740,437   6/1973  Harrison ...................... 260/473 F X
3,770,774  12/1973  Jenkins .......................... 260/340.5

Primary Examiner—Ethel G. Love
Attorney, Agent, or Firm—Lawrence S. Levinson; Merle J. Smith; Stephen B. Davis

[57]                ABSTRACT
Compounds are provided having the structure:

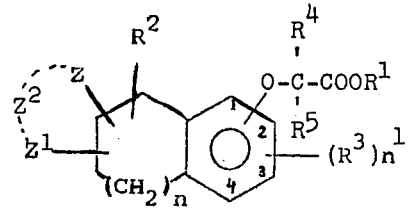

and to salts of such compounds. These compounds are useful as hypocholesteremic agents and anti-inflammatory agents.

5 Claims, No Drawings

NAPHTHYLOXY ACETIC ACIDS AND RELATED COMPOUNDS

This application is a division of serial no. 305,619 filed on November 10, 1972, now U.S. Pat. No. 3,906,032.

This invention relates to compounds of the structure:

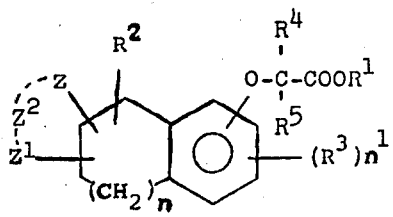

wherein $R^1$ can be hydrogen, lower alkyl, cycloalkyl, monocyclic aryl and aralkyl, $R^2$ can be hydrogen, lower alkyl or aralkyl, $R^3$ can be hydrogen, lower alkyl, aralkyl, lower alkoxy, carboxy, monocyclic cycloalkyl, alkenyl, halogen, acyl, amino, acylamino, nitro, dihydroalkyl, or $R^6O(CH_2)n^2$- where $R^6$ is hydrogen, lower alkyl or aralkyl, $n$ is 0, 1 or 2, $n^1$ is 0, 1 or 2; and $n^2$ is 0 to 10, $R^4$ and $R^5$ can be the same or different and can by hydrogen, lower alkyl, cycloalkyl, monocyclic aryl or aralkyl.

In formula I, the group

II 

may or may not include a $Z^2$ group.

Where $Z^2$ is not present in the formula I compounds, the present invention includes compounds of the structure:

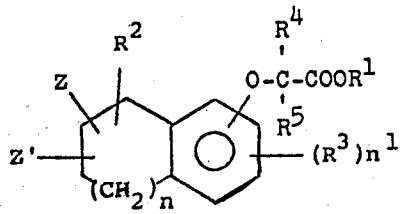

wherein Z and $Z^1$ can be the same or different and can be $R^7$-X- and $R^8$-Y-, respectively, formyl cyano, azido or

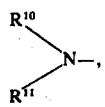

wherein X and Y can be

—$(CH_2)_n3$- wherein $n^3$ is 1 to 8, —O—, —S—,

or

where $R^9$ is hydrogen, lower alkyl, aralkyl or acyl, and $R^{10}$ and $R^{11}$ are as defined hereinafter and $R^7$ and $R^8$ can be the same or different and can be hydrogen, lower alkyl, aryl, acyl, alkoxy, hydroxy, $$\underset{R^{11}}{\overset{R^{10}}{\diagdown}} N-,$$

alkynyl or alkenyl.

Where a $Z^2$ group is present, the present invention includes compounds of the formula:

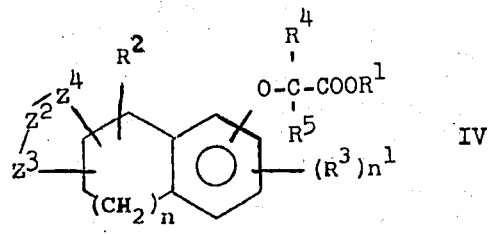

wherein $Z^3$-$Z^2$-$Z^4$ together with two carbons of the cycloalkyl ring form a 5- or 6-membered ring, $Z^3$ and $Z^4$ may be the same or different and can be —$CH_2$-, =N-, -O-, -S-, -$NR^{14}$-, -O-$CH_2$—, -S-$CH_2$-, or -$NR^9$-$CH_2$- where $R^{14}$ is hydrogen, lower alkyl or aryl, $Z^2$ can be

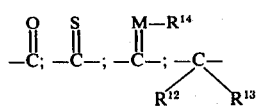

where $R^{12}$ and $R^{13}$ can be hydrogen, lower alkyl, cycloalkyl, aryl, haloalkyl, amino ($R^{10}R^{11}N$) or aminoalkyl;

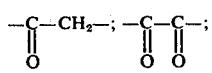

and $Z^3$-$Z^2$-$Z^4$- can be taken together to form

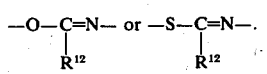

The term "lower alkyl" as employed herein includes both straight and branched chain radicals of up to and including eight carbon atoms, for instance, methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl and the like.

The term "aralkyl" includes groups such as benzyl, phenethyl as well as any of the aryl groups mentioned below attached to any of the above lower alkyl groups.

The term "lower alkoxy" includes straight and branched chain radicals of the structure RO- wherein R includes any of the above lower alkyl groups.

The terms "alkenyl" and "alkynyl" refer to aliphatic groups containing three to eight carbons and one double or one triple bond such as allyl, and any of the isomers of butenyl, pentenyl, hexenyl, heptenyl, octenyl, ethynyl, butynyl and the like.

The term "halogen" includes F, Br, Cl or I.

Alkyl radicals substituted by one to three halogen atoms such as F, Br, Cl or I are encompassed by the term halo-lower alkyl. Trifluoromethyl is a preferred halo-lower alkyl radical.

The "amino" groups include unsubstituted amino or mono- or di-lower alkyl-amino groups, wherein lower alkyl is as defined above, such as amino, methylamino, ethylamino, isopropylamino, heptylamino, dimethylamino, diethylamino, methylethylamino, methylbutylamino, ethyl i-propylamino and the like.

The "acyl" radicals are derived from hydrocarbon carboxylic acids of up to fifteen carbons and include lower fatty acid radicals such as acetyl, propionyl, butyryl, isobutyryl and the like, as well as long chain fatty acid radicals such as hexanoyl, heptanoyl, decanoyl, dodecanoyl and the like, monocyclic aryl and aralkanoic acid radicals such as benzoyl, phenacetyl and the like.

The term "monocyclic aryl" as employed herein contemplates monocyclic carbocyclic aryl radicals, for instance, phenyl and substituted phenyl radicals, such as lower alkyl or lower alkoxy phenyl (e.g., o-, m- or p-tolyl, ethylphenyl, butylphenyl, methoxyphenyl, ethoxyphenyl and the like), di(lower alkyl)phenyl (e.g., 2,4-dimethylphenyl, 3,5-diethylphenyl and the like), halophenyl (e.g., chlorophenyl, bromophenyl, iodophenyl, fluorophenyl), o-, m- or p-nitrophenyl, dinitrophenyl, (e.g., 3,5-dinitrophenyl, 2,6-dinitrophenyl and the like), and trinitrophenyl (e.g., picryl).

The terms "monocyclic cycloalkyl" includes cyclic radicals containing from 3 to 6 ring members (e.g., cyclopropyl, cyclobutyl, cyclopentyl and cyclohexyl).

In the basic nitrogen containing radical

$R^{10}$ and $R^{11}$ each represents hydrogen, lower alkyl, lower alkenyl, hydroxy-lower alkyl and phenyl-lower alkyl forming such basic groups as amino, lower alkylamino, e.g., methylamino, ethylamino, isopropylamino, di(lower alkyl)amino, e.g., dimethylamin diethylamino, dipropylamino, lower alkenylamino, e.g., allylamino, di(lower alkenyl)amino, e.g., diallylamino, (hydroxy-lower alkyl)amino, e.g., hydroxyethylamino, di(hydroxy-lower alkyl)amino e.g., di(hydroxyethyl)amino, phenyl(loweralkyl)amino, e.g., benzylamino, phenethylamino, N-(lower alkyl)phenyl(lower alkyl)amino, e.g., N-methylbenzylamino, and the like.

The

radical may form a heterocyclic radical. The symbols $R^{10}$ and $R^{11}$ may together represent the carbon (and hydrogen) and the oxygen, sulfur or nitrogen atoms which, with the nitrogen or carbon atom in the above group, form a 5- or 6-membered nitrogen heterocyclic containing not more than one hetero atom in addition to the nitrogen already shown in the group and less than 21 atoms in the radical (excluding hydrogen). The heterocyclic radicals may include one to three substituents including lower alkoxy or lower alkyl as defined hereinbefore; trifluoromethoxy; trifluoromethylmercapto; N,N-dialkylsulfamoyl groups, such as N,N-dimethylsulfamoyl; lower alkanoyl groups

where R is lower alkyl) as defined hereinbefore, such as acetyl, propionyl, and the like; hydroxy-lower alkyl, such as hydroxymethyl, 2-hydroxyethyl or the like; hydroxy-lower alkoxy-lower alkyl, such as 2-(2-hydroxy-ethoxy)ethyl, or the like; lower alkanoyl-lower alkyl, such as 2-heptanoyloxyethyl; carbo-lower alkoxy, such as carbomethoxy, carboethoxy, carbopropoxy, or the like; or 2-(lower alkanoyloxy-lower alkoxy)lower alkyl such as 2-(decanoyloxyethoxy)ethyl, or the like.

Illustrative of the heterocyclic radicals represented by

are the following: piperidino; (lower alkyl)piperidino [e.g., 2-, 3-, or 4-(lower alkyl)piperidino or 4-(N-lower alkyl)piperidino, such as 2-(ethyl)piperidino or 4-(N-isopropyl)piperidino]; di(lower alkyl)piperidino [e.g., 2,4-, 2,5- or 3,5-di(lower alkyl)piperidino, such as 2,4-dimethyl piperidino or 2,5-di-t-butyl piperidino]; (lower alkoxy)piperidino [e.g., 2-methoxypiperidino or 3-methoxypiperidino]; hydroxypiperidino [e.g., 3-hydroxy- or 4-hydroxypiperidino]; aminomethylpiperidino [e.g., 4-aminomethylpiperidino]; pyrrolidino; (lower alkyl)pyrrolidino [e.g., 3-methylpyrrolidino]; di(lower alkyl)pyrrolidino [e.g., 3,4-dimethylpyrrolidino]; (lower alkoxy)pyrrolidino [e.g., 2-methoxypyrrolidino]; morpholino; (lower alkyl)morpholino [e.g., 3-methylmorpholino]; di(lower alkyl)morpholino, [e.g., 3,5-dimethylmorpholino]; (lower alkoxy)morpholino, [e.g., 2-methoxymorpholino]; thiamorpholino; (lower alkyl)thiamorpholino [e.g., 3-methylthiamorpholino]; di(lower alkyl)thiamorpholino, [e.g., 3,5-dimethylthiamorpholino], (lower alkoxy)thiamorpholino, [e.g., 3-methoxythiamorpholino]; piperazino; (lower alkyl)piperazino, [e.g., $N^4$-methylpiperazino]; di(lower alkyl)piperazino, [e.g., 2,5-dimethylpiperazino or 2,6-dimethylpiperazino]; (lower alkoxy)piperazino, [e.g., 2-methoxypiperazino]; (hydroxy-lower alkyl)piperazino, [e.g., $N^4$-(2-hydroxyethyl)piperazino]; (lower alkanoyloxy-lower alkyl)piperazino, [e.g., $N^4$-(2-heptanoyloxyethyl)piperazino or $N^4$-(2-propionyloxyethyl)piperazino]; (hydroxy-lower alkoxy-lower alkyl)-piperazino, [e.g., (hydroxymethoxymethyl)-piperazino]; (carbo-lower alkoxy)piperazino, [e.g., $N^4$-(carbomethoxy-, carboethoxy-, or carbopropoxy)-piperazino]; piperidyl; (lower alkyl)piperidyl [ e.g., 1-, 2-, 3- or 4-(lower alkyl)piperidyl, such as 1-N-methylpiperidyl or 3-ethylpiperidyl]; di(lower alkyl)piperidyl, [e.g., 2,4-, 2,5-, or 3,5-di(lower alkyl) piperidyl wherein lower alkyl is methyl, ethyl, n-propyl, isopropyl, etc.]; lower alkoxy piperidyl, [e.g., 3-methoxypiperidyl or 2-ethoxypiperidyl]; hydroxypiperidyl [e.g., 3-hydroxy- or 4-hydroxypiperidyl]; aminomethylpiperidyl, [e.g., 4-aminomethylpiperidyl]; pyrrolidyl; lower alkyl pyrrolidyl, [e.g., 1-N-methylpyrrolidyl]; di(lower alkyl)pyrrolidyl, [e.g., 2,3-dimethylpyrrolidyl]; lower alkoxy pyrrolidyl, [e.g., 4-N-methoxypyrrolidyl]; morpholinyl; (lower alkyl)morpholinyl, [e.g., 3-methylmorpholinyl]; di(lower alkyl)morpholinyl, [e.g., 3-methyl-4-N-ethylmorpholinyl]; (lower alkoxy)-morpholinyl, [e.g., 2-ethoxymorpholinyl]; thiamorpholinyl; (lower alkyl)thiamorpholino, [e.g., 3-ethylthiamorpholinyl]; di(lower alkyl)thiamorpholinyl, [e.g., 3-methyl-4-N-ethylthiamorpholinyl]; lower alkoxy thiamorpholino, [e.g., 3-methoxythiamorpholinyl]; piperazinyl; alkyl, dialkyl, alkoxy or hydroxy-lower alkyl substituted piperazinyl.

The compounds of formula I were $Z^2$ is not present and one or both of Z or $Z^1$ is an amine form acid addition salts with inorganic and organic acids. In addition, where $Z^2$ is present and $Z^2$, $Z^3$, $Z^4$ or $R^3$ includes a basic nitrogen, the compounds of formula I also form acid addition salts with such acids. These acid addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic or organic acid. Illustrative are the hydrohalides, especially the hydrochloride and hydrobromide which are preferred, sulfate, nitrate, phosphate, borate, acetate, oxalate, tartrate, maleate, citrate, succinate, benzoate, ascorbate, salicylate, methanesulfonate, benzenesulfonate, toluenesulfonate, and the like. Quaternary ammonium salts are also formed, e.g., by reacting the free base with an alkylating agent, e.g., lower alkyl halide such as methyl chloride, ethyl bromide, or the like, lower alkyl sulfate such as methyl sulfate, aralkyl halides such as benzyl chloride, aralkyl sulfates such as benzyl sulfate, and the like.

The compounds of formula I, when $R^1$ is hydrogen, form basic salts with inorganic and organic bases. These salts frequently provide useful means either for solubilizing the acid or for isolating the products from reaction mixtures by forming the salt in a medium in which it is insoluble. The free acid may be obtained from the salt by neutralization, e.g., with an acid such as hydrochloric acid, dilute sulfuric acid, phosphoric acid or the like. Then any other salt may again be formed from the free acid and the appropriate inorganic or organic base. Illustrative are alkali metal salts, e.g., sodium, potassium, etc., alkaline earth metal salts, e.g., calcium, magnesium, etc., aluminum salts, ammonium salts as well as salts with organic bases such as choline, benzylamine, triethylamine, cyclohexylamine and the like.

Preferred are those compounds where the oxyacetic acid group is in the 1- or 2- position, more preferably in the 1-position; where $Z^2$ is not present, it is preferred that Z and $Z^1$ each are hydroxyl, $R^2$ and $R^3$ are hydrogen, $R^4$ and $R^5$ are methyl and $R^1$ is hydrogen or lower alkyl; where $Z^2$ is present, it is preferred that Z and $Z^1$ each are oxygen, $Z^2$ is

where $R^{12}$ and $R^{13}$ are hydrogen or lower alkyl, $R^2$ and $R^3$ are each hydrogen, $R^4$ and $R^5$ are each methyl and $R^1$ is hydrogen or lower alkyl.

The compounds of formula I may be produced by the following method.

A phenolic compound of the structure:

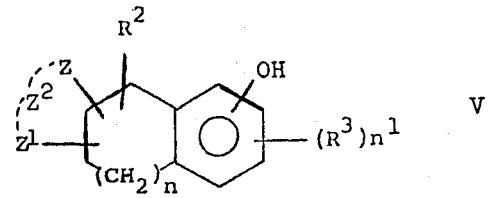

V is made to react with a haloester of the formula:

VI wherein Q is halogen, preferably bromine, and $R^{1'}$ is lower alkyl, cycloalkyl, phenyl or benzyl in the presence of a base like potassium hydroxide, sodium hydride, sodamide or potassium t-butoxide to obtain a product of the formula:

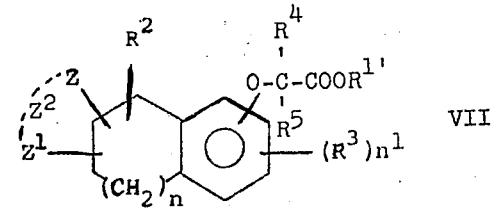

VII

Heating the compound of formula VII with an alcohol solution of an alkali metal hydroxide, e.g., potassium hydroxide or sodium hydroxide in methanol or ethanol, e.g., for about 0.5 to 3 hours, yields a product of formula I, where $R^1$ is hydrogen in appropriate cases after neutralization.

The starting phenolic compounds of formula V can be a bicyclic compound having the following structure where $Z^2$ is not present:

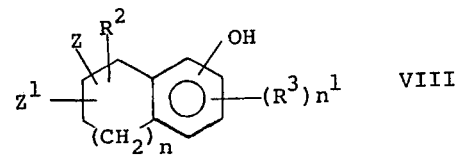

VIII

These compounds of formula VIII, including methods of preparation therefor, are fully disclosed in copending application, Ser. No. 268,314, filed July 3, 1972, now abandoned, entitled Substituted Cyclic Polymethylene Phenols.

For example, compounds of formula VIII wherein Z and $Z^1$ are hydroxy and n is one, that is

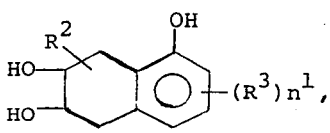

X

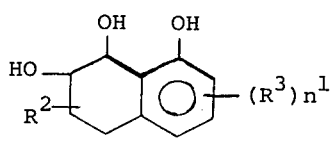

XI or

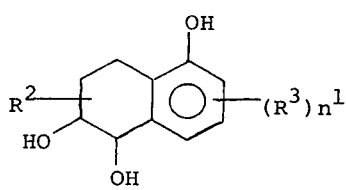

XII can be prepared by dissolving a compound of the structure

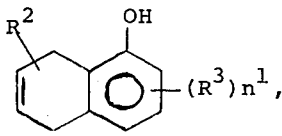

XIII

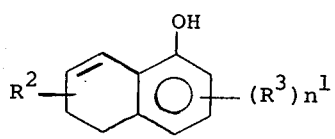

XIV or

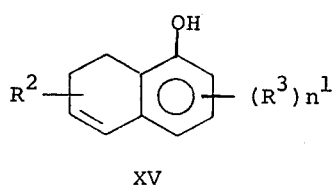

XV in acetic acid and water (from 92 to 98% acetic acid, preferably 96% acetic acid), and then treating the solution with silver acetate and iodine and heating under nitrogen and subjecting the product to basic hydrolysis. The stereochemical relationship of the hydroxyls thus introduced varies depending upon the amount if any of water present during the reaction.

The 5,8-dihydro-1-naphthol of formula XIII is prepared by reducing a naphthol of the structure

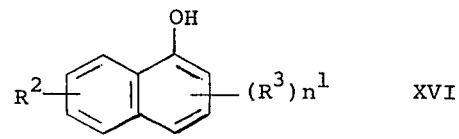

XVI with a metal such as sodium or lithium in liquid ammonia containing an alkanol such as ethanol, isopropanol, t-butanol or the like [e.g. by the procedure described in Organic Synthesis, Coll. Vol. 4, page 887 (1963)].

Treatment of the 5,8-dihydro-1-naphthol of formula XIII with a base, such as an alkali metal hydroxide and refluxing under nitrogen, cooling and thereafter acidifying the cooled mixture yields the compounds of formulae XIV and XV.

Compounds of formula VIII, wherein n is 0, and Z and $Z^1$ are hydroxy, that is compounds of the formula

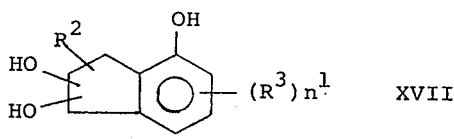

XVII may be prepared by reacting a compound of the formula

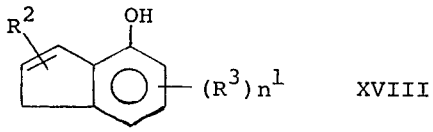

XVIII (as disclosed in Japanese Patent No. 082,297 (11/9/69)/072582) (Derwent No. 83217 R-B) with a benzyl halide, such as benzyl chloride, in a base such as an alkali metal alkoxide, such as sodium methoxide, in the presence of a solvent such as dimethyl sulfoxide, to form compounds of the structure

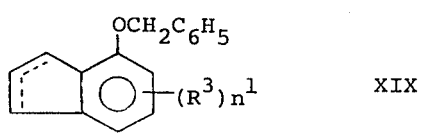

XIX wherein the dashed lines indicate the presence of a single double bond in varied position, which can be reacted with hydrogen peroxide in the presence of an acid, such as acetic acid, to form compounds of the structure

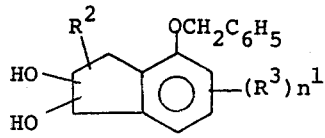                                                     XX

Compound of formula VIII wherein n is 2 and Z and $Z^1$ are hydroxy, and $R^3$ is methoxy, that is compounds of the formula

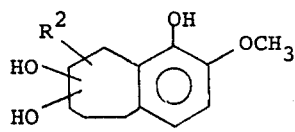                                                     XXI can be prepared by reducing compounds of the structure

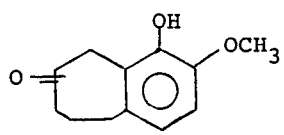                                                     XXII as disclosed in J. Org. Chem. 25 131 (1960), for example, by reacting it with a reducing agent such as sodium borohydride in an alcohol solvent, to form compounds of the structure

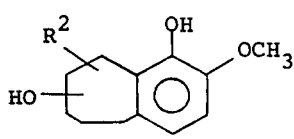                                                     XXIII

The above mono-hydroxy compounds can be reacted with hydrochloric acid in acetic acid to form compounds of the structure

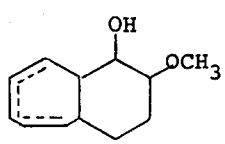                                                     XXIV which can be converted to the corresponding compounds or other derivatives as described with respect to the indanols and naphthols.

It will be appreciated that compounds of the invention wherein Z and $Z^1$ are other than hydrogen and the OH group is in the 2-position or β-position may be prepared as described above hereinbefore with respect to the compounds of the invention wherein OH is in the 1- or α-position, employing as starting materials, compounds where OH is in the 2- or β-position.

The starting phenolic compounds of formula V can be a tricyclic compound, where $Z^2$ is present, having the structure:

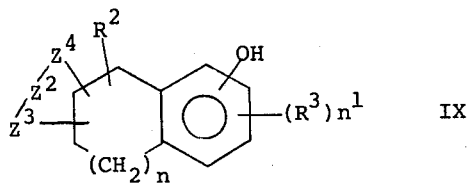                                                     IX

The compounds of formula IX, including methods of preparation therefor, are fully disclosed in copending application, Ser. No. 268,300, filed July 3, 1972, entitled Tricyclic Tetrahydro Naphthaleneols and Related Compounds.

Examples of haloesters which can be employed herein include, but are not limited to the following as set out in Table A below.

Table A $$Q-\underset{R^5}{\overset{R^4}{C}}-COOR''$$

| Q | $R^4$ | $R^5$ | $R''$ |
|---|---|---|---|
| Br | $C_6H_5$ | $CH_3$ | $C_2H_5$ |
| Br | [S] | H | $CH_3$ |
| Cl | $CH_3$ | $CH_3$ | $CH_3$ |
| Br | $C_6H_5CH_2-$ | $CH_3$ | $C_2H_5$ |
| Br | $C_2H_5$ | $C_2H_5$ | $C_2H_5$ |
| Br | H | H | $C_2H_5$ |
| Br | H | $CH_3$ | $C_2H_5$ |
| Br | $CH_3$ | $CH_3$ | $C_2H_5$ |
| Br | $C_3H_7$ | $C_2H_5$ | $CH_3$ |
| Cl | H | H | $C_2H_5$ |
| Br | $C_4H_9$ | H | $C_2H_5$ |
| Br | $C_6H_5$ | H | $C_2H_5$ |

The symbols in all of the foregoing formulas have the same meanings previously defined.

The new compounds of this invention are useful as hypocholesteremic agents. They inhibit cholesterol biosynthesis and regulate the cholesterol in the blood of warm-blooded animals such as rats or the like. Thus they are useful in the treatment of conditions such as atherosclerosis. The compounds of the invention may be administered orally or parenterally, e.g., at a dosage level of 2 to 40 mg/kg/day in single or divided doses, preferably 4 to 10 mg/kg orally two to four times daily, in the form of tablets, capsules, elixirs, injectables, or the like by compounding up to about 300 mg. of a substance of formula I or a physiologically acceptable salt thereof together with a suitable vehicle, excipient, lubricant, flavor, etc., according to accepted pharmaceutical practice.

The new compounds of this invention are also useful as anti-inflammatory agents, for example, to reduce local inflammatory conditions such as those of an edematous nature, in various animals such as rats, dogs and the like, when given orally in dosages of about 5 to 50 mg/kg/day, preferably 5 to 25 mg/kg/day, in single or 2 to 4 divided doses, as shown by the carageenan edema assay in rats. The compound may be utilized in compositions containing up to about 300 mg. of a compound of Formula I or a physiologically acceptable salt thereof made up in conventional manner with vehicle or carrier for oral administration to animals as indicated above. Topically, compositions containing up to about 1% by weight in a conventional cream may be used.

The following Examples are illustrative and represent preferred embodiments of the invention. All temperatures are on the Centigrade scale.

EXAMPLE 1 cis-2-[(6,7-Dihydroxy-5,6,7,8-tetrahydro-1-naphthyl)oxy]-2-methylpropionic acid, ethyl ester Sodium hydride, 50% (0.75 mole) is added in portions with stirring to 50 ml. of cooled absolute ethyl alcohol. After the evolution of hydrogen has subsided, 0.075 mole of 6,7-dihydroxy-5,6,7,8-tetrahydro-1-naphthol is added, followed by the dropwise addition of 0.075 mole of ethyl α-bromoisobutyrate. The reaction mixture is refluxed with stirring for 16 hours. The solvent is evaporated in vacuo, the residue taken up in water and extracted with chloroform. The chloroform extract is washed with water, dried and freed of solvent to give the title compound in the form of an oil.

EXAMPLE 2 cis-2-[(6,7-Dihydroxy-5,6,7,8-tetrahydro-1-naphthyl)oxy]-2-methylpropionic acid

To a solution of 0.05 mole of the product of Example 1 in 50 ml. of methyl alcohol, 30 ml. of 40% methanolic potassium hydroxide is added and the mixture is refluxed for 0.5 hours. The solvent is removed in vacuo, the residue dissolved in water, acidified and extracted with chloroform. The chloroform extract is washed with water, dried and concentrated to give the title compound as a thick oil.

EXAMPLE 3

2-[6,7-Dihydroxy-5,6,7,8-tetrahydro-1-naphthyl)oxy]-acetic acid ethyl ester

Following the procedure of Example 1, but substituting an equivalent amount of ethyl bromoacetate for the ethyl α-bromoisobutyrate, there is obtained the title compound.

EXAMPLE 4

α-[(6,7-Dihydroxy-5,6,7,8-tetrahydro-1-naphthyl)oxy]-2-methylpropionic acid, ethyl ester, 6,7-acetonide
A. cis-5,6,7,8-Tetrahydro-1,6,7-naphthalenetriol A solution of 29.2 g. (0.2 mole) of 5,8-dihydro-1-naphthol and 40 ml. of acetic anhydride in 100 ml of pyridine is prepared. After 16 hr. the solvent is removed in vacuo and the residue dissolved in ether and washed with 200 ml. of 5% hydrochloric acid, water, 200 ml. of 10% sodium hydroxide, saturated salt solution and dried. Solvent removal gives 34.2 g (90.5%) of crude acetate which is dissolved in 900 ml. of acetic acid and 36 ml. of water. 53.3 g. (0.32 mole) of silver acetate is added followed by 40.6 g. (0.16 g-atom) of iodine. The slurry is heated with good stirring at 85°± 10° for 3 hr. under nitrogen, cooled and filtered. The filtrate is evaporated in vacuo and the residue dissolved in 250 ml. of methanol and cooled to 0°. A solution of 40 g. of sodium hydroxide in 200 ml. of water is added under nitrogen and the mixture stirred overnight. The bulk of the methanol is removed in vacuo whereupon a solid forms. The solid is separated by filtration, dissolved in 150 ml. of water and acidified with 20 ml. of concentrated hydrochloric acid. Cooling gives a solid which is filtered and dried to give 16.5 g. 2,3 cis-5,6,7,8-tetrahydro-1,6,7-naphthalenetriol m.p. 184.5-187°. Three recrystallizations from absolute ethanol give the analytical sample, m.p. 188°–188.5°.

Anal. Calc'd for $C_{10}H_{12}O_3$: C, 66.65; H, 6.71; Found: C, 66.19; H, 6.68.

B. Acetonide of cis-5,6,7,8-tetrahydro-1,6,7-naphthalenetriol

A slurry of 5.4 g of the cis-5,6,7,8-tetrahydro-1,6,7-naphthalene-triol in 50 ml of 2,2-dimethoxy propane is treated with 150 mg. of TsOH (solution in 10 min). After 1 hr. the solution is partitioned between ether and sat'd bicarbonate solution. The organic layer is dried and evaporated to give 6.58 g. essentially TLC homogeneous. Crystallization of a small sample from hexane/ethyl acetate gives the title material of mp. 130.5-131.5°.

C. 2-[6,7-Dihydroxy-5,6,7,8-tetrahydro-1-naphthyloxy]-2-methylpropionic acid, ethyl ester, 6,7-acetonide Following the procedure of Example 1 but substituting the acetonide of the triol of part B above for the 1-naphthol, the title compound is obtained.

EXAMPLE 5

$O^6,O^7$-Butylidene-2-[6,7-dihydroxy-5,6,7,8-tetrahydro-1-naphthyl)-oxy]-2-methylpropionic acid ethyl ester A. A solution of 3.6 g (0.02 moles) of the triol of Example 1 in 50 ml. of benzene, and 1.5 g of butanal in the presence of 0.1 g p-toluene sulfonic acid are mixed together and stirred for several hrs. Water is removed by azeotropic distillation and the residue is taken to dryness to yield $O^6$, $O^7$-butylidene - 5,6,7,8-tetrahydro-1,6,7-naphthalene triol.

B. $O^6$, $O^7$-Butylidene-2-[6,7-dihydroxy-5,6,7,8-tetrahydro-1-naphthyl)oxy]-2-methylpropionic acid ethyl ester The procedure of Example 1 is repeated employing the triol of part A to form the title compound.

EXAMPLE 6

$O^6$, $O^7$-β-Diethylaminoethylidene-2-[6,7-dihydroxy-5,6,7,8-tetrahydro-1-naphthyl)oxy]-phenylacetic acid methyl ester A. 6,7-β-chloroethylidene-5,6,7,8-tetrahydro-1,6,7-naphthalenetriol A solution of 27 g (0.15 moles) of cis-5,6,7,8-tetrahydro-1,6,7-naphthalenetriol prepared as described in Example 1 in 250 ml of benzene and 25 g of diethoxyethyl chloride in the presence of 0.2 g p-toluene sulfonic acid are mixed together for several hours. Water is removed by azeotropic distillation and the residue taken to dryness to yield the title compound.

B. $O^6,O^7$-β-Diethylaminoethylidene-5,6,7,8-tetrahydro-1,6,7-naphthalenetriol

The procedure described in J. Pharm and Pharmac. 23, 649 (1971) is followed.

The haloacetal from part A is dissolved in ethanol containing excess diethylamine and the mixture heated at 100°C for 48 hours in a bomb. The mixture is cooled and water and solvent stripped therefrom. The residue is purified by chromatography on Alumina II neutral to yield the title compound.

C. $O^6,O^7$-β-Diethylaminoethylidene-2[6,7-dihydroxy-5,6,7,8-tetrahydro-1-naphthyl)oxy]-phenylacetic acid methyl ester The procedure of Example 1 is followed employing the triol of part B and

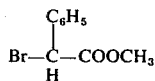

to form the title compound.

EXAMPLE 7

2-[6,7-Dihydroxy-5,6,7,8-tetrahydro-1-naphthyl)oxy]-2-methylpropionic acid ethyl ester $O^6,O^7$-cyclic carbonate A. 5,8-Dihydro-1-naphthol, benzyl ether A solution of 5,8-dihydro-1-naphthol (73 g., 0.5 M) in 400 ml. DMSO is treated with 0.5 M of sodium methoxide. The mixture is cooled in an ice bath while benzyl bromide (85.5 g., 0.5 M) is added dropwise. The mixture has to be shaken periodically since there is difficulty in stirring. Toward the end of the addition the mixture is allowed to warm to ~45°, and stirring is continued for 2–3 hours after addition is complete. The mixture is then poured into 1 liter $H_2O$ and the product is extracted into ether. The ether extracts are washed with 10% NaOH, dried and the solvent is removed in vacuo to give a quantitative yield of crude crystalline product.

A small sample (4 g.) of this is recrystallized twice from methanol to give the title compound, 1.3 g., mp 70-74°.

Anal. Calc'd for $C_{17}H_{16}O$: C, 86.40; H, 6.83; Found: C, 86,58; H, 6.6.

B. cis-5,6,7,8-tetrahydro-1,6,7-naphthalenetriol-$O^1$-benzyl ether

To 47.2 g (0.20 mole) of the above ether dissolved in 900 ml of acetic acid containing 30 ml of water is added 53.3 g (0.32 mole) of silver acetate with vigorous stirring followed by 40.6 g (0.16 g. atom) of iodine. After 1 hour, the slurry is heated to 85-95° for 3 hours under nitrogen, cooled and filtered. The filtrate is taken to dryness in vacuo and the residue taken up in 250 ml of methanol and treated in the cold with a solution of 40 g of sodium hydroxide in 200 ml of water. After stirring overnight, the bulk of the methanol is removed in vacuum, and the product extracted into chloroform. After drying and solvent removal, the product is induced to crystallize by trituration with hexane.

C. 5,6,7,8-tetrahydro-1,6,7-naphthalenetriol-$O'$-benzyl-ether-$O^6,O^7$-carbonate In accordance with the procedure set out in Arch. Pharm. 304 590 (1971), a solution of 27 g (0.1 mole) of the diol of part B (0.1 m) in 200 ml of THF is treated with 1.7 g. (0.1 m) of N,N-carbonyl diimidazole and heated under reflux for 2 hrs. After cooling, the mixture is poured into water and the product extracted into $CHCl_3$, dried and purified on deactivated silica gel to give the title compound.

D. 2-[6,7-Dihydroxy-5,6,7,8-tetrahydro-1-naphthyl)oxy]-2-methylpropionic acid ethyl ester $O^6,O^7$-cyclic carbonate The procedure of Example 1 is repeated employing the above carbonate and

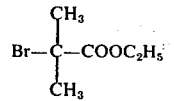

to form the title compound.

EXAMPLE 8

$O^6,O^7$-2'-Butylidene-2[6,7-dihydroxy-5,6,7,8-tetrahydro-2-naphthyl)oxy]-2-methyl propionic acid ethyl ester A. 5,8-Dihydro-2-naphthol The procedure of Marshall, et al, Can. J. Chem., 47. 3127 (1969) is followed exactly. From 25.0 g of β-naphthol is obtained 18.9 g of crude product. NMR analysis indicated it to contain ca. 40% of the desired 5,8-dihydro-2-naphthol and 60% of 5,6,7,8-tetrahydro-2-naphthol.

B. cis-5,6,7,8-Tetrahydro-2,6,7-naphthalene triol

The 18.9 g. of crude product was converted to the acetate by the procedure used in Example 1 and the resulting oil (23.8 g) was heated at 90° for 3 hr. with 300 ml. of acetic acid, 20 ml. of water, 23.5 g. of silver acetate and 18.0 g. of iodine. The slurry was cooled and filtered. The filtrate was evaporated and the residue stirred overnight under nitrogen with 100 ml. each of water and methanol and 20 g. of sodium hydroxide. The methanol was removed in vacuo and the residue acidified at 0° with 155 ml. of 12% hydrochloric acid. The oil which separated crystallized when shaken in a

15 separatory funnel with chloroform. Filtration gave 7.9 g. of tan solid. Recrystallization from ethanol/ethyl acetate gave in several crops 4.03 g., mp 193-195.5°.

C. $O^6,O^7$-2'-Butylidene-5,6,7,8-tetrahydro-2,6,7-naphthalenetriol

Following the procedure of Example 5 substituting for butanal, methyl ethyl ketone, the title compound is obtained.

D. $O^6,O^7$-2'-Butylidene-2-[6,7-dihydroxy-5,6,7,8-tetrahydro-2-naphthyl)oxy]-2-methylpropionic acid ethyl ester Following the procedure of Example 1 employing the above triol and

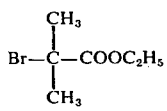

the title compound is formed.

EXAMPLE 9

S,O-Isopropylidene-2-[6(and 7)mercapto-7(and 6)hydroxy-5,6,7,8-tetrahydro-1-naphthyl)oxy]-2-methylpropionic acid ethyl ester A. 6,7-Epoxy-5,6,7,8-tetrahydro-1-naphthyl benzyl ether A solution of 73 g. (0.5 m) of 5,8-dihydro-1-naphthol in 100 ml. DMSO is treated with 0.5 m sodium methoxide. The mixture is cooled in an ice bath and treated dropwise with 0.5 mole benzyl bromide with shaking periodically. The mixture is gradually allowed to warm up to about 45° toward the end of addition. The mixture is stirred 3 hrs. longer, then poured into 1 liter H₂O and extracted into ether. Extracts are washed twice with 10% NaOH, dried, taken to dryness leaving almost a quantitative yield of crystalline 5,8-dihydro-1-naphthyl benzyl ether.

A solution of 23.6 g. (0.10 m) of the above ether in 250 ml. CHCl₃ is treated with a solution of 0.11 m m-chloroperbenzoic acid in CHCl₃ at 10°-15°C and stirred overnight. After filtration, the organic filtrate is washed with dilute K₂CO₃, dried and freed of solvent, leaving crude solid epoxy ether.

B. 7(and 6)Mercapto-5,6,7,8-tetrahydronaphthalene-1,6(and 7)diol

A solution of the above epoxyether (12.6 g, 0.05 m) in ethanol was added to an aqueous solution of sodium sulfide and the resulting mixture warmed for several hours. After cooling and acidification with acetic acid, the product was extracted into CHCl₃, debenzylated, dried and freed of solvent to leave a mixture of isomeric mercapto alcohols of structure:

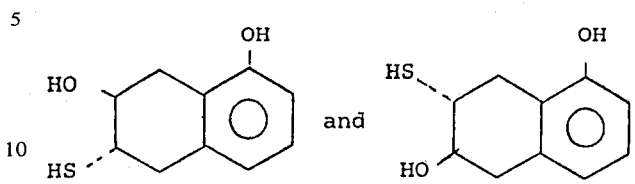

C. Acetonide of 7(and 6)mercapto-5,6,7,8-tetrahydronaphthalene-1,6(and 7)diol

In a manner similar to Example 4B, substituting the above mercapto compounds from part B for the triol, the title acetonide is obtained.

S,O-Isopropylidene-2-[6 (and 7)mercapto-7 (and 6)hydroxy-5,6,7,8-tetrahydro-1-naphthyl)oxy]-2-methyl propionic acid ethyl ester The procedure of Example 1 is followed employing the above acetonide to form the title compound.

EXAMPLE 10

2-[3a,4,9,9a-Tetrahydro-2-butyl-2-methyl-2H-naphtho(2,3-d)-1-thia-3-oxol-5(and 8)yl)oxy]-2-methylpropionic acid ethyl ester A. S,O-2'-Hexylidene-6(and 7) mercapto-5,6,7,8-tetrahydronaphthalene-1,7 (and 6) diol Employing the mercaptan prepared in Example 9B in lieu of the 1,2,3,4-tetrahydro-1,2,5-naphthalenetriol in the procedure of Example 5, and replacing the butanal with methyl butyl ketone, the following compound is obtained

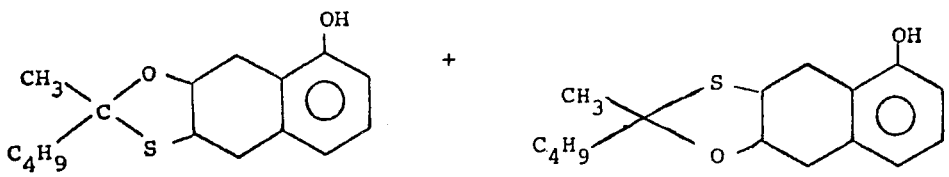

B. 2-[3a,4,9,9a-Tetrahydro-2-butyl-2-methyl-2H-naphtho-(2,3-d)-1-thia-3-oxol-5 (and 8)yl)oxy]-2-methylpropionic acid ethyl ester The procedure of Example 1 is followed employing the above diol to form the title compound.

EXAMPLE 11

2-[3a,4,9,9a-Tetrahydro-2-diethylaminomethyl-2H-naphtho(2,3-d)-1-thia-3-oxol-5 (and 8)yl)oxy]-phenylacetic acid methyl ester A. S,$O^7$-β-Chloroethylidene-6-mercapto-5,6,7,8-tetrahydronaphthalene-1,7-diol Employing the mercaptan prepared in Example 9B in lieu of cis-5,6,7,8-tetrahydro-1,6,7-naphthalenetriol in the procedure of Example 6A, the following compound is obtained.

B. 2-[3a,4,9,9a-Tetrahydro-2-diethylaminomethyl-2H-naphtho-(2,3-d)-1-thia-3-oxol-5 (and 8)yl)oxy]-phenylacetic acid methyl ester The procedure of Example 6C is followed employing the above compound to form the title compound.

EXAMPLE 12

2-[3a,4,9,9a-Tetrahydro-2H-naphtho(2,3-d)-1-thia-3-oxol-2-one-5 (and 8)yl)oxy]-2-methylpropionic acid ethyl ester A. 6-Mercapto-5,6,7,8-tetrahydronaphthalene-1,7-diol S,O⁷-carbonate-O'-benzyl ether Employing the benzyl ether of the mercaptan of Example 9B in the procedure of Example 4 in lieu of the diol, the following compound is obtained.

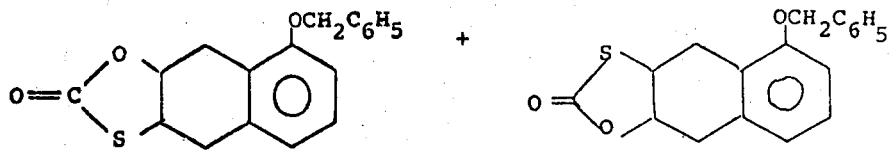

B. 2-[3a,4,9,9a-Tetrahydro-2H-naphtho(2,3-d)-1-thia-3-oxol-2-one-5(and 8)yl)oxy]-2-methylpropionic acid ethyl ester The above compound is debenzylated by reaction with Pd/C in the presence of pyridine and the resulting phenol is subjected to the procedure of Example 1 to form the title compound.

EXAMPLE 13

7-Hydroxy-1(and 4)-(2'-carbethoxy-2'-propoxy)-5,6,7,8-tetrahydro-6-naphthyloxyacetic acid lactone A. 7(and 6)Hydroxy-5,6,7,8-tetrahydro-6(and 7)-naphthyloxyacetic-acid lactone The above compound is prepared by reacting 0.1 mole 5,6,7,8-tetrahydro-1,6,7-naphthalenetriol 0'-benzyl ether with 0.1 mole of Cl-CH₂CO₂C₂H₅ in 100 ml of dimethoxyethane in the presence of 3 g NaH and heating the mixture at reflux for several hours and thereafter separating the product from the reaction mixture by chromatography on silica gel.

Catalytic debenzylation over 5% Pd/c in ethanol then affords the free phenol.

B. 7-Hydroxy-1(and 4)-(2'-carbethoxy-2'propoxy)-5,6,7,8-tetrahydro-6-naphthyloxyacetic acid lactone The procedure of Example 1 is followed employing the above phenol to form the title compound.

EXAMPLE 14

2-[6,7-Dihydroxy-5,6,7,8-tetrahydro-1-naphthyl)oxy]-2-methylpropionic acid ethyl ester 0⁶,0⁷-cyclic oxalate A. 5,6,7,8-Tetrahydronaphthalene-1,6,7-triol 0⁶, 0⁷-cyclic oxalate-O'benzyl ether The above compound is prepared by dissolving 0.1 m of 5,6,7,8-tetrahydro-1,6,7-naphthalenetriol 0'-benzyl ether in 25 ml of cold pyridine and adding 0.1 m of oxalyl chloride dropwise. After filtration and solvent removal, the product is purified by chromatography on silica gel. Catalytic debenzylation over 5% Pd on C then yields the free phenol.

B. 2-[6,7-Dihydroxy-5,6,7,8-tetrahydro-1-naphthyl)oxy)-2-methylpropionic acid ethyl ester 0⁶, 0⁷ cyclic oxalate The procedure of Example 1 is followed employing the above phenol to form the title compound.

EXAMPLE 15

2-[(3a,4,9,9a-Tetrahydro-2H-naphtho(2,3-d)-1-thia-3-oxol-2-thion-5(and 8)yl)oxy]-2-methylpropionic acid ethyl ester A. 6-Mercapto-5,6,7,8-tetrahydro-naphthalene-1,7-diol-0'-benzyl ether 0⁷, S-thiocarbonate The procedure of Examples 9 and 4 are followed employing the benzyl ether of the mercaptan of Example 9B and thiophosgene in place of phosgene to form the above compound.

B. 2-[(3a,4,9,9a-Tetrahydro-2H-naphtho(2,3-d)-1-thia-3-oxol-2-thion-5(and 8)yl)oxy]-2-methylpropionic acid ethyl ester Catalytic debenzylation of the benzyl ether over 5% Pd on C in the presence of ethanol yields the free phenol. The free phenol is subjected to the procedure of Example 1 to form the title compound.

EXAMPLE 16

2-[(3a,4,9,9a-Tetrahydro-2H-naphtho(2,3-d)-1-oxy-3-azol-2-one-5(and 8)yl)oxy]-2-methylpropionic acid ethyl ester A. 6(and 7)-Amino-5,6,7,8-tetrahydronaphthalene-1,7-(and 6)-diol-0'-benzyl ether 0⁷,N-carbonate A solution of 0.1 m each of the epoxide benzyl ether of Example 9A and phenyl isocyanate in xylene is added to a solution containing 0.004 m of tributyl phosphine oxide and 0.003 m of lithium bromide in xylene and the mixture heated under reflux overnight. After cooling, solvent is removed and the crude mixture of products purified on neutral Alumina III to give the title compound.

Method Ref. Tet. Letters 809 (1971)

B. 2-[(3a,4,9,9a-Tetrahydro-2H-naphtho(2,3-d)-1-oxy-3-azol-2-one-5(and 8)yl)oxy]-2-methylpropionic acid ethyl ester Catalytic debenzylation of the benzyl ether over 5% Pd on C in the presence of ethanol yields the free phenol. The free phenol is subjected to the procedure of Example 1 to form the title compound.

EXAMPLE 17

2-[3a,4,9,9a-Tetrahydro-2H-naphtho(2,3-d)-1-oxa-3-azol-2-thion-5(and 8)yl)oxy]-2-methylpropionic acid ethyl ester A. 6-Amino-5,6,7,8-tetrahydronaphthalene -1,7-diol-0'-benzyl ether 0⁷,N-thiocarbonate A solution of 0.1 m each of the epoxide benzyl ether of Example 9A and butylisothiocyanate in xylene added to a solution containing 0.004 m of tributyl phosphine oxide and 0.003 m of lithium bromide in xylene and the mixture heated under reflux overnight. After cooling, solvent is removed and the crude mixture of products purified on neutral Alumina III to give the title compound.

Method Ref. Tet. Letters 809 (1971).

B. 2-[3a,4,9,9a-Tetrahydro-2H-naphtho(2,3-d)-1-oxa-3-azol-2-thion-5-(and 8)yl)oxy]-2-methylpropionic acid ethyl ester Catalytic debenzylation of the above benzyl ether over 5% Pd on C in the presence of ethanol yields the free phenol. The free phenol is subjected to the procedure of Example 1 to yield the title compound.

EXAMPLE 18

2-[3a,4,9,9a-Tetrahydro-2-phenyl-1H-naphth(2,3-d)oxazol-5-(and 8)yl)oxy]-2-methylpropionic acid ethyl ester A. 6,7-Epoxy-5,6,7,8-tetrahydro-1-naphthol benzyl ether A solution of 12.8 (0.054 m) of 5,7-dihydro-1-naphthol benzyl ether in 150 ml of $CH_2Cl_2$ was cooled to 0° and 8.9 g 0.052 mole of m-chloroperbenzoic acid was added over a period of 5 min. and the mixture was stirred overnight at room temperature.

The suspension was poured into a mixture of 50 ml of 10% NaOH and 100 g of ice. The aqueous layer was extracted with $CH_2Cl_2$, and the combined organic layers were washed with water and satd. NaCl soln. dried and evaporated in vacuo to give the title compound.

B. trans 6(and 7)-Amino-5,6,7,8-tetrahydro-1,7(and 6)-naphthalenediol

A solution of 6,7-epoxy-5,6,7,8-tetrahydro-1-naphthol 0'-benzyl ether 12.6 g (0.05 mole) in 200 ml dioxane was heated to 40° and a solution of sodium azide (6.8 g, 0.11 mole) in water (20 ml) was added dropwise. The mixture was heated under reflux overnight, cooled, filtered and the solvent was removed in vacuo.

The crude azide was dissolved in 100 ml of ether and added to a suspension of LAH (5 g) in 250 ml of ether. After several hours at reflux, the mixture was decomposed with aqueous potassium carbonate and the filtrate freed of solvent.

C. C-Phenylimidazole derivative of 6-amino-5,6,7,8-tetrahydronaphthalene-1,7-diol 0'-benzyl ether The trans amino alcohol was converted to its N-benzoyl derivative with benzoyl chloride-pyridine. This is added portionwise to excess thionyl chloride and then kept at 50°–60° for 3 hrs. Removal of excess reagent in vacuum leaves the crude cis oxazoline as its HCl salt, which is recrystallized from ethanol-ether.

D. 2-[3a,9,9,9a-Tetrahydro-2-phenyl-1H-naphth(2,3-d)-oxazol-5-(and 8)yl)oxy]-2-methylpropionic acid ethyl ester Catalytic debenzylation of the above benzyl ether over 5% Pd/C in the presence of ethanol yields the free phenol which is converted to the title compound by the procedure of Example 1.

EXAMPLE 19

2-[3a,4,9,9a-Tetrahydro-2-amino-1H-naphth(2,3-d)oxazol-5-(and 8)yl)oxy]-2-methylpropionic acid ethyl ester A. Aminooxazoline derivative of 6(and 7)amino-5,6,7,8-tetrahydronaphthalene-1,7(and 6)diol An intimate mixture of 12.6 g. (0.05 mole) of 6,7-epoxy-5,6,7,8-tetrahydro-1-naphthyl benzyl ether and 25 g. of guanidine are heated to 140°–180°C until gas evolution ceases. The reaction mixture is cooled, and the product recrystallized from alcohol.

B. 2-[3a,4,9,9a-Tetrahydro-2-amino-1H-naphth(2,3-d)oxazol-5-(and 8)yl)oxy]-2-methylpropionic acid ethyl ester The free phenol obtained on catalytic debenzylation is subjected to the procedure of Example 1 to form the title compound.

EXAMPLE 20

6-Hydroxy-5(and 8)-(2'-carbethoxy-2'-propoxy)5,6,7,8-tetrahydronaphthalene-7-acetic acid lactone A. 1,7(and 6)Dihydroxy-5,6,7,8-tetrahydro-6(and 7)naphthaleneacetic acid lactone A solution of 12.6 g (0.05 mole) of 6,7-epoxy-5,6,7,8-tetrahydronaphthol benzyl ether and 7.5 g (0.05 mole) of diethylmalonate in 150 ml of absolute ethanol containing about 0.01 mole of sodium ethoxide was brought to reflux for several hours. The mixture was cooled, treated with concentrated HCl and warmed to effect hydrolysis and decarboxylation. Removal of the solvent left crude lactone which was purified by chromatography on silica gel.

Catalytic debenzylation over 5% Pd on C in ethanol provided the free phenol.

B. 6-Hydroxy-5(and 8)-(2'-carbethoxy-2'-propoxy)5,6,7,8-tetrahydronaphthalene-7-acetic acid lactone The procedure of Example 1 is followed employing the above phenol to form the title compound.

EXAMPLE 21

6-Mercapto-5(and 8)-(2'-carbethoxy-2'-propoxy)-5,6,7,8-tetrahydronaphthalene-7-acetic acid thiolactone A. 7(and 6)Mercapto-1-hydroxy-5,6,7,8-tetrahydronaphthalene acetic acid lactone Employing 6,7-epithio-5,6,7,8-tetrahydronaphthol benzyl ether in place of the epoxide in Example 20A produced the title compound.

B. 6-Mercapto-5(and 8)-(2'-carbethoxy-2'-propoxy)-5,6,7,8-tetrahydronaphthalene-7-acetic acid thiolactone The procedure of Example 1 is followed employing the above lactone to form the title compound.

EXAMPLE 22

2-[6,7-Dihydroxy-5,6,7,8-tetrahydro-1-naphthyl)oxy]-2-methylpropionic acid ethyl ester 6,7-acetonide The product of Example 1 is dissolved in acetone in the presence of a catalytic amount of p-toluene sulfonic acid and the mixture is refluxed to form the title compound, identical to the material prepared in Example 4.

EXAMPLE 23

2-[5-Methoxy-6-hydroxy-5,6,7,8-tetrahydro-1-naphthyl)oxy]-2-methylpropionic acid ethyl ester A. 5,6- and 7,8-dihydro-1-naphthol A mixture of 105.8 g of crude 5,8-dihydro-1-naphthol and 480 g of 50% sodium hydroxide was refluxed under nitrogen for 2 hr, poured onto 2 kg of ice and acidified with conc. hydrochloric acid. The solid was taken up in ether, the ether dried and evaporated and the residue distilled to give 88 g, bp 91°–95° at 0.05 mm. Four recrystallizations from 400 ml of hexane gave 59 g, mp 70.5–76° which contained ca. 10–15% of 5,6,7,8-tetrahydro-1-naphthol in addition to the two olefins. VPC and NMR showed the absence of 5,8-dihydro-1-naphthol and 1-naphthol.

B. Epoxidation of 5,6- and 7,8-dihydro-1-naphthyl acetate.

A solution of 18.4.g (0.10 mole) of the acetate of the above mixture (prepared with pyridine and acetic anhydride) in 400 ml of methylene chloride was cooled to 0° and 20.0 g (ca. 0.1 mole) of commercial m-chloroperbenzoic acid added. After 2 hr at 0°100 ml of cold 6% sodium hydroxide was added with good stirring. After 5 min the layers were separated and the organic layer dried and evaporated to give 19.8 g of oil.

The above 19.8 g of epoxide was dissolved in 400 ml of methanol and stirred overnight with 200 mg of TsOH. The solution was cooled to 0° and 100 ml of 9% sodium hydroxide added. After 2 hr at 0° the bulk of the methanol was removed in vacuo and 75 ml of 10% hydrochloric acid added at 0°. Extraction with chloroform (5×200 ml) gave 19.2 g of oil which showed five major spots on TLC ($CHCl_3$, alumina, $I_2$) coded A-E in order of decreasing $R_f$. This material was absorbed onto 150 ml neutral Alumina II, placed on a 550 g column of dry packed Alumina II and eluted with: 1400 ml of 1:1 hexane/$CHCl_3$, 700 ml 2:1 $CHCl_3$/hexane, 700 ml of 3:1 $CHCl_3$/hexane, 600 ml of $CHCl_3$, and 1500 ml of 5% methanol in $CHCl_3$ (100 ml fractions).

Fractions 1-6 contained 2.38 g of TLC pure A, identical by mp and TLC to 5,6,7,8-tetrahydro-1-naphthol.

Fractions 9–12 contained 0.63 g of TLC pure B, identical by TLC and IR to the starting olefin mixture.

Fractions 15–21 contained 1.68 g of C that is cis-8-methoxy-5,6,7,8-tetrahydro-1,7-naphthalenediol contaminated with the by-product D. Recrystallization from ethyl acetate gave 812 mg of TLC pure C, mp 131°–135.5°.

Fractions 22-28 contained 2.13 g of D contaminated with E, that is trans-5-methoxy-5,6,7,8-tetrahydro-1,6-naphthalenediol. Recrystallization from ethyl acetate gave 1.36 g of TLC pure D, mp 110.5°–113°.

Fractions 29-51 contained 8.33 g of E with small amounts of contaminants which are removed by recrystallization from ethyl acetate to give 4.79 g of TLC pure E. mp 137.5°–139°.

C. 2-[5-Methoxy-6-hydroxy-5,6,7,8-tetrahydro-1-naphthyl)oxy]-2-methylpropionic acid ethyl ester The procedure of Example 1 is followed employing trans-5-methoxy-5,6,7,8-tetrahydro-1,6-naphthalenediol(E) to form the title compound.

EXAMPLE 24

2-[8-Methoxy-7-hydroxy-5,6,7,8-tetrahydro-1-naphthyl)oxy]-2-methylpropionic acid ethyl ester The procedure of Example 1 is followed employing cis-8-methoxy-5,6,7,8-tetrahydro-1,7-naphthalenediol (Product C described above in Example 23B) to form the title compound.

EXAMPLE 25 trans-2-[6,7-dihydroxy-5,6,7,8-tetrahydro-1-naphthyl)oxy]-2-methylpropionic acid ethyl ester
A. trans-1,2,3,4-Tetrahydro-5-acetoxy-1,2-naphthalenediol.

A solution of 41.3 g of the epoxy acetate (prepared in overall 73% yield from 5,8-dihydro-1-naphthol as described in Example 23B in 420 ml of THF and 105 ml of water was cooled to 0° and 2.4 ml of 70% $HClO_4$ added. After 150 min at 0° the solution was partitioned between 600 ml of ether and a mixture of 600 ml of sat'd salt and 100 ml of sat'd sodium bicarbonate solution. The organic layer was separated, dried and evaporated to give 46.2 g of oily solid. Trituration with 200 ml of boiling ether gave 13.4 g, mp 153-158°. Recrystallization from 250 ml of ethyl acetate gave 10.2 g, mp 161°-162.5°, homogeneous on TLC.

B. trans-1,2,3,4,-Tetrahydro-1,2,5-naphthalenetriol.

A solution of 13.3 g of the above acetate in 500 ml of THF was cooled to 0° and 140 ml of 1 N sodium hydroxide solution added under nitrogen. After 2 hr at 0°, carbon dioxide was bubbled through to pH = 8, the slurry diluted with 1 liter of sat'd salt and the mixture extracted with $CHCl_3$ (3 × 500 ml) to give 9.1 g of solid. Recrystallization from 100 ml of ethyl acetate gave 5.7 g. mp 147.5–149.5°.

C. trans-2-[6,7-dihydroxy-5,6,7,8-tetrahydro-1-naphthyl)oxy]-2-methylpropionic acid ethyl ester The procedure of Example 1 is followed employing the triol of part B to form the title compound.

EXAMPLE 26

2-[7-Hydroxy-6-isopropylamino-5,6,7,8-tetrahydro-1(and 4)-naphthyl)oxy]-2-methylpropionic acid ethyl ester A. 6,7-Epoxy-5,6,7,8-tetrahydro-1-naphthol acetate.

A solution of 101 g (0.542 M) of 5,8-dihydro-1-naphthol acetate in 1.5 liters of $CH_2Cl_2$ was cooled to 0° and 89 g (0.516 M) of m-chloroperbenzoic acid was added over a period of 5 min. and the mixture was stirred overnight at room temperature.

The suspension was poured into a mixture of 500 ml of 10% NaOH and 1000 g of ice. The aqueous layer was extracted with $CH_2Cl_2$ (2 × 500 ml), and the combined organic layers were washed with water and satd. NaCl soln, dried and evaporated in vacuo to give the title compound, 105 g (95% yield) of pink solid.

B. 6,7-trans-5,6,7,8-Tetrahydro-7(and 6)-(isopropylamino)-1,6(and 7)-naphthalenediol, hydrochloride.

A mixture of epoxy acetate (10.2 g; 0.05 M) and isopropylamine was charged to the small bomb and heated overnight in an oil bath maintained at 100°. After cooling, the excess amine was removed in vacuo leaving a dark brown viscous material which was chromatographed on activity 3 neutral alumina. Fractions eluted with 10-20% MeOH in $CHCl_3$ yielded crystalline material on standing under hexane. Two recrystallizations from ether gave a sample melting 112°–117°. This was dissolved in IPA-ether and converted to the hydrochloride by adding a solution of HCl in IPA. The white hydrochloride was recrystallized from IPA-MeOH-ether to give isomers of the above name, 2.2 g (17%), mp 207-210°C.

Anal. Calcd for $C_{13}H_{20}O_2NCl$: C, 60.57; H, 7.82; N, 5.43; Cl, 13.75; Found: C, 60.81; H, 7.72; N, 5.24; Cl, 13.61.

C. 2-[7-Hydroxy-6-isopropylamino-5,6,7,8-tetrahydro-1(and 4)-naphthyl)oxy]-2-methylpropionic acid ethyl ester The procedure of Example 1 is followed employing the diol of part B to form the title compound.

EXAMPLE 27

2-[6-Benzylamino-7-hydroxy-5,6,7,8-tetrahydro-1(and 4)naphthyl)-oxy]-2-methylpropionic acid ethyl ester
A. trans-6(and 7)-(benzylmethylamino)-5,6,7,8-tetrahydro1,7(and 6)-naphthalenediol A mixture of 6,7-epoxy-5,6,7,8-tetrahydro-1-naphthol acetate (10.2 g, 0.05 M) prepared in Example 26A, methyl benzylamine (50 g) and xylene (50 ml) is heated under reflux overnight. After cooling the solution is taken to dryness in vacuo and the dark brown viscous material remaining is chromatographed on silica gel (Davison Grade 923, 100–200 mesh). Fractions eluted with 1–5% MeOH in $CHCl_3$, containing 11.0 g (~76%), show a single spot on TLC (silica gel, developed 2% MeOH in $ChCl_3$). Ether is added to these fractions and after standing a small amount of crystalline material is deposited. This is harvested (1.6 g) and recrystallized from ether to give the title compound 1.15 g (8%), mp 152°–154°C.

Anal. Calcd for $C_{18}H_{21}O_2N$: C, 76.29; H, 7.47; N, 4.94. Found: C, 76.24; H, 7.69; N, 4.75.

B. 2-[6-Benzylamino-7-hydroxy-5,6,7,8-tetrahydro-1(and 4)-naphthyl)oxy]-2-methylpropionic acid ethyl ester The procedure of Example 1 is followed employing the diol of part B to form the title compound.

EXAMPLE 28

2-[6-Amino-7-hydroxy-5,6,7,8-tetrahydro-1(and 4)naphthyl)oxy]-2-methylpropionic acid ethyl ester A. trans-6(and 7)-amino-5,6,7,8-tetrahydro-1,7(and 6)-naphthalenediol A solution of 6,7-epoxy-5,6,7,8-tetrahydro-1-naphthol acetate (20.4 g, 0.1 M), prepared as in Example 26A, in 200 ml. dioxane is heated to 40° and a solution of sodium azide (6.8 g, 0.11 M) in water (20 ml) is added dropwise. The mixture is heated under reflux overnight, cooled, filtered and the solvent is removed in vacuo.

The crude azide is dissolved in ethanol, platinum oxide (~ 1 g) is added and the mixture is hydrogenated at up to 45 psi for 20 hrs. During this time the bottle is vented and refilled with hydrogen six times. The catalyst is removed by filtration and washed with ethanol. The filtrate is taken to dryness in vacuo, hexane is added and crystalline product is removed by filtration (13.1 g, 73%). A 3.0 g sample of this is recrystallized twice from ethyl acetate methanol to give the title compound, 1.5 g (37%), mp 172-193°dec.

Anal. Calcd for $C_{10}H_{13}NO_2$: C, 67.02; H, 7.31; N, 7.82. Found: C, 67.24; H, 7.33; N, 7.84.

B. 2-[6-Amino-7-hydroxy-5,6,7,8-tetrahydro-1(and 4)-naphthyl)oxy]-2-methylpropionic acid ethyl ester The procedure of Example 1 is followed employing the above diol to form the title compound.

EXAMPLE 29

2-[6,7-Dihydroxy-5,6,7,8-tetrahydro-2-naphthyl)oxy]-2-methylpropionic acid ethyl ester A. 5,8-Dihydro-2-naphthol The procedure of Marshall, et al, Can. J. Chem., 47, 3127 (1969) is followed exactly. From 25.0 g of β-naphthol is obtained 18.9 g of crude product. NMR analysis indicates it to contain ca. 40% of the desired 5,8-dihydro-2-naphthol and 60 % of 5,6,7,8-tetrahydro-2-naphthol.

B. cis-5,6,7,8-Tetrahydro-2,6,7-naphthalene triol.

The 18.9 g of crude product of part A is converted to the acetate by reaction with acetic anhydride in the presence of pyridine and the resulting oil (23.8 g) is heated at 90° for 3 hr with 300 ml of acetic acid, 20 ml of water, 23.5 g of silver acetate and 18.0 g of iodine. The slurry is cooled and filtered. The filtrate is evaporated and the residue stirred overnight under nitrogen with 100 ml each of water and methanol and 20 g of sodium hydroxide. The methanol is removed in vacuo and the residue acidified at 0° with 155 ml of 12% hydrochloric acid. The oil which separates crystallizes when shaken in a separatory funnel with chloroform. Filtration gives 7.9 g of tan solid. Recrystallization from ethanol/ethyl acetate gives in several crops 4.03 g. mp 193°–195.5°.

C. 2-[6,7-Dihydroxy-5,6,7,8-tetrahydro-2-naphthyl)oxy]-2-methylpropionic acid ethyl ester The procedure of Example 1 is followed employing the above triol to form the title compound.

EXAMPLE 30

2-[(2-Piperidino-5-indanyl)oxy]-2-methylpropionic acid ethyl ester

A. 2-Piperidino-5-indanol

A 2.8 g (0.013 moles) sample of 5-amino-2-piperidinoindan was taken up in 100 ml of 5% sulfuric acid and clarified by filtering through a Hy-Flo pad. The clear yellow solution was cooled in ice and treated over 5 minutes with a solution of 0.9 g (0.013 moles) sodium nitrite in 20 ml of water. The cold mixture was stirred at 0°–5°C for one-half hr, then added over 40 minutes to 400 ml of vigorously boiling 5% sulfuric acid. After refluxing another one-half hr the mixture was cooled to room temperature and treated with solid potassium carbonate until $CO_2$ evolution ceased. Methylene chloride was added and the brown solid which collected at the interface was retrieved by filtration and washed with water. (This material was soluble in dilute sodium hydroxide). The solid was suspended in hot absolute ethanol and evaporated to dryness. Crystallization from ethyl acetate gave 1.8 g (64%) brown crystals, mp 246-247°C. Norit treatment and crystallization afforded the 1.3 g analytical sample of 2-piperidino-5-indanol, a bright yellow solid, mp 243°–246°C.

Anal. Calcd for $C_{14}H_{19}NO$: C, 77.38; H, 8.81; N, 6.45
Found: C, 77.46; H, 9.08; N, 6.79

B. 2-[(2-Piperidino-5-indanyl)oxy]-2-methylpropionic acid ethyl ester

The procedure of Example 1 is followed employing the above indanol to form the title compound.

EXAMPLE 31

2-[2-Hydroxy-5-indanyl)oxy]-2-methylpropionic acid ethyl ester

A. 2-Indanol

A 60 g sample of 2-indanone (0.45 moles) in 1.5 liters of 40% aqueous methanol was treated with 18 g (0.46 moles) of sodium borohydride in portions with cooling to maintain T ≤ 40°C. After the addition was complete (15 min), the mixture was stirred for 2 hrs then allowed to stand overnight at room temp. Ether extraction, drying over potassium carbonate and evaporation gave 58.3 g crystalline 2-indanol (96%).

B. 4- and 5-Nitro-2-acetoxyindan

A slurry of 6.7 g (0.05 moles) of 2-indanol in 75 ml acetic anhydride was cooled to −15°C (ice-acetone bath) and treated with 0.2 ml of 98% sulfuric acid. In about 10 minutes the solid had completely dissolved. The stirred and cooled mixture was then treated over 15 min with a cold solution of 3.6 ml (5.0 g) of 70% nitric acid in 125 ml of acetic anhydride. The mixture was stored at −20°C overnight, then poured into 1 kg of crushed ice. The mixture was stirred until the ice had completely melted and most of the anhydride had reacted. The mixture was extracted with 500 ml of hexane. The organics were washed with saturated bicarbonate and evaporated to 3.0 g of an oil which solidified on standing. Trituration with hexane and recrystallization from the same solvent gave 1.1 g of 2-acetoxy-5-nitroindan, mp 84°–85°C. The aqueous from the hexane extraction yielded 5.3 g of an oil on extraction with benzene. All but 0.9 g of this oil went into hot hexane. Cooling to room temperature gave some oil. The mother liquor was decanted and cooled to 5°C overnight to give 2.0 g (35% total) of the 5-nitro compound, mp 82°–84°C. The filtrate was concentrated to 100 ml cooled again and filtered to give another 0.4 g crude 5-nitro, mp 60°–74°C. The mother liquors were concentrated but gave no solid on cooling. Evaporation afforded 2.0 g (22%) of oily 2-acetoxy-4-nitroindan, contaminated with some 4-nitroindene.

C. 5-Amino-2-acetoxyindan

A slurry of 8.0 g (0.045 moles) of 2-acetoxy-5-nitroindan in 25 ml of absolute ethanol and 32 ml of concentrated hydrochloric acid was treated over 1 hr with a solution of 24 g (0.11 moles) of stannous chloride in 32 ml of absolute ethanol, with water bath cooling to maintain T=20°C. The mixture was stirred for 1 day at room temperature, diluted with 100 ml of water and extracted twice with ether. The aqueous phase was basified with 10% sodium hydroxide until the hydroxides redissolved, then extracted with chloroform, dried (sodium sulfate) and evaporated to an oil which crystallized to 3.9 g (82%) 5-amino-2-hydroxyindan, the hydrochloride of which had mp 237°–239° after one crystallization from ether-methanol isopropanol.

D. 2,5-Dihydroxyindan 3.9 g (0.026 moles) amine were dissolved in 130 ml 5% $H_2SO_4$ and filtered through Hy-Flo. The solution was cooled in an ice bath and a solution of 1.99 g (0.0288 moles) $NaNO_2$ in 20 ml $H_2O$ added over 5 min with stirring (T ≤ 5°C). After stirring for one-half hr at 0°c, urea (0.2 g) was added and solution stirred for another 10 min at 0°C. with stirring. This cold solution was added to 400 ml vigorously boiling 5% $H_2SO_4$ over 2 hrs. This was refluxed for an additional 1/2 hr and cooled to room temperature. A small amount of brown solid was filtered off, and the filtrate extracted with $CHCl_3$. Organics were dried ($MgSO_4$) and evaporated (0.4 g). The aqueous was extracted with n-BuOH. Organic were dried ($MgSO_4$) and evaporated (15 g).

The brown solid, $CHCl_3$ and n-BuOH extracts were combined and chromatographed on 300 g basic alumina (Act III) in $CHCl_3$. Elution with 5% MeOH in $CHCl_3$ yielded 2.5 g crystalline phenol, mp 112°–115°C.

A portion recrystallized twice from ethylacetate-hexane had mp 116°–118°C.

E. 2-[2-Hydroxy-5-indanyl)oxy]-2-methylpropionic acid ethyl ether

The procedure of Example 1 is followed employing the indan of part D to form the title compound.

EXAMPLE 32

2-[6-Hydroxy-7-methylamino-5,6,7,8-tetrahydro-1(and 4)naphthyl)oxy]-2-methylpropionic acid ethyl ester A. 5,8-Dihydro-1-naphthol, benzyl ether A solution of 5,8-dihydro-1-naphthol (73 g, 0.5 M) in 400 ml DMSO was treated with 0.5 M of sodium methoxide. The mixture was cooled in an ice bath while benzyl bromide (85.5 g, 0.5 M) was added dropwise. The mixture had to be shaken periodically since there was difficulty in stirring. Toward the end of the addition the mixture was allowed to warm to ~45°, and stirring was continued for 2–3 hrs after addition was complete. The mixture was then poured into 1 liter $H_2O$ and the product was extracted into ether. The ether extracts were washed with 10% NaOH, dried and the solvent was removed in vacuo to give a quantitative yield of crude crystalline product.

A small sample (4g) of this was recrystallized twice from methanol to give the benzyl ether, 1.3 g, mp 70°–74°.

Anal. Calcd for $C_{17}H_{16}O$: C, 86.40; H, 6.83

Found: C, 86.58; H, 6.60

B. 6,7-Epoxy-5,6,7,8-tetrahydro-1-naphthol, benzyl ether

The dihydro benzyl ether (47 g, 0.2 M) was dissolved in 200 ml chloroform and treated with a chloroform solution of 50 g m-chloroperbenzoic acid which was added dropwise over a period of 1 hour. The mixture was stirred overnight at room temperature. A small amount of insoluble material was then removed by filtration and the filtrate was poured into dil. $K_2CO_3$ solution. After stirring a few minutes the layers were separated and the chloroform solution was dried over $K_2CO_3$, filtered, and the solvent was removed in vacuo leaving a quantitative yield of crude epoxide.

C. trans-3-(Benzylmethylamino)-5-(and 8)-benzyloxy-1,2,3,4-tetrahydro-2-naphthol.

A mixture of the crude epoxide (10 g, 0.042 M) and methylbenzyl amine (35 g) in 125 ml toluene was heated under reflux overnight. After cooling the reaction mixture was taken to dryness in vacuo leaving 15.2 g of dark brown oil. This was chromatographed on activity 2 neutral alumina. Fractions eluted with benzene-chloroform and chloroform crystallized on standing. These contained 6.0 g (38% yield). Part of this material was recrystallized twice from ether to give the title compound, 400 mg, mp 126-136°.

Anal. Calcd for $C_{25}H_{27}O_2N$: C, 80.39; N, 7.29; N, 3.75

Found: C, 80.64; N, 7.11; N, 3.78

D. trans-3-(Methylamino)-5-(and 8)-hydroxy-1,2,3,4-tetrahydro-2-naphthol

The compound of part C is catalytically debenzylated over 5% Pd on C in acetic acid to yield the title compound.

E. 2-[6-Hydroxy-7-methylamino-5,6,7,8-tetrahydro-1(and 4)naphthyl)oxy]-2-methylpropionic acid ethyl ester The procedure of Example 1 is then followed employing the diol of part D to form the title compound.

EXAMPLE 33

2-[(6,7-Epimino-5,6,7,8-tetrahydro-1-naphthyl)oxy]-2-methylpropionic acid ethyl ester A. 6,7-Epimino-5,6,7,8-tetrahydro-1-naphthyl benzyl ether To an ether solution of iodine isocyanate (formed by reaction of 25.4 g (0.1 m) $I_2$ and 20 g (0.13 m) silver cyanate) is added 0.1 m of 5,8-dihydro-1-naphthyl benzyl ether over one-half hour. After stirring several hours, the mixture is filtered and treated with anhydrous methanol plus a little lithium methoxide. After standing in the dark overnight it is refluxed briefly then taken to near dryness in vacuum. The residual liquid is poured into ice-water containing a little sodium sulfide and extracted with ether. After washing with saturated salt solution, the ether solution of the iodo isocyanate is treated with 40% aqueous sodium bisulfite and stirred.

The crude bisulfite addition product is dissolved in 2N NaOH in methanol and heated under reflux for 3 hours poured into salt solution and extracted with ether. Evaporation of the dried ether leaves the desired epimino compound.

Ref: Hassner et al. JOC 32 540 (1967).

B. 6,7-Epimino-5,6,7,8-tetrahydro-1-naphthol

Careful debenzylation of the above epimino compound is conducted in a mixture of ammonia and alcohol using 2.1 equivalents of lithium. After the ammonia has evaporated, the pH is adjusted with acetic acid and the product extracted into chloroform, washed, dried and freed of solvent.

C. 2-[(6,7-Epimino-5,6,7,8-tetrahydro-1-naphthyl)oxy]-2-methylpropionic acid ethyl ester The procedure of Example 1 is then followed employing the epiminophenol of part B to form the title compound.

EXAMPLE 34

2-[(6,7-Epithio-5,6,7,8-tetrahydro-1-naphthyl)oxy]-2-methylpropionic acid ethyl ester A. 6,7-Epithio-5,6,7,8-tetrahydronaphthyl benzyl ether To 0.125 mole of potassium thiocyanate in 20 ml. of 50% ethanol is added 0.10 mole of 6,7-epoxy-5,6,7,8-tetrahydro-1-naphthyl benzyl ether and the mixture stirred vigorously for 48 hours. The product is extracted into ether, washed with salt solution, dried and freed of solvent. Ref: O.S. IV 232.

B. 6,7-Epithio-5,6,7,8-tetrahydro-1-naphthol

Careful debenzylation is then carried out to yield the desired phonol.

C. 2-[(6,7-Epithio-5,6,7,8-tetrahydro-1-naphthyl)oxy]-2-methylpropionic acid ethyl ester The procedure of Example 1 is then followed employing the epithio compound of part B to form the title compound.

EXAMPLE 35

2-[(6-Mercapto-5,6,7,8-tetrahydro-1(and 4)-naphthyl)oxy]-2-methylpropionic acid ethyl ester A. 6-Mercapto(or 7-mercapto)-5,6,7,8-tetrahydro-1-naphthol To an ether solution of 0.25 m lithium alluminum hydride in 200 ml $Et_2O$ is added dropwise a solution of 5.36 g (0.02 m) of the episulfide of Example 34 in 50 ml of dioxane. After refluxing overnight the mixture is decomposed with $K_2CO_3$ solution and the inorganics removed by filtration. Evaporation of the filtrates leaves crude mercaptan. This is taken up in ether, added to liquid ammonia and treated with 0.05 mole of lithium in small pieces. After removal of ammonia the residue is taken up in water and acidified. Product is extracted into $CHCl_3$, dried, and freed of solvent. The mixture of mercaptans is then chromatographed on silica gel to effect separation of 6- and 7-mercapto-5,6,7,8-tetrahydro-1-naphthol.

B. 2-[(6-Mercapto-5,6,7,8-tetrahydro-1(and 4)-naphthyl)oxy]-2-methylpropionic acid ethyl ester The procedure of Example 1 is followed employing the mercapto compound of part A to form the title compound.

EXAMPLE 36

2-[(6-Mercapto-7-methoxy-5,6,7,8-tetrahydro-1(and 4)-naphthyl)oxy]-2-methylpropionic acid ethyl ester A. 6(and 7)Mercapto-7(and 6)methoxy-5,6,7,8-tetrahydro-1-naphthol A solution of 5.36 g (0.02 m) of the episulfide of Example 34 in 100 ml of methanol is treated with a few drops of perchloric acid and heated to reflux for several hours. The mixture is diluted with water and the products extracted into chloroform. Solvent removal leaves a mixture of the isomeric products which is separated on silica. The separated isomeric products are then debenzylated to give the title compounds.

B. 2-[(6-mercapto-7-methoxy-5,6,7,8-tetrahydro-1(and 4)-naphthyl)oxy]-2-methylpropionic acid ethyl ester Following the procedure of Example 1, employing the 1-naphthol compound of part A, the title compound is obtained.

EXAMPLE 37

2-[(6-Hydroxy-7-methylthio-5,6,7,8-tetrahydro-1-naphthyl)oxy]-2-methylpropionic acid ethyl ester A. 6,7-trans-5,6,7,8-Tetrahydro-7(or 6)-(methylthio)-1,6(or 7)-naphthalenediol To a solution of 5 g (0.2 m) Na in 150 ml EtOH is added 20.4 g (0.1 m) of the epoxy acetate of Example 4A followed by 15 g (~0.3 m) $CH_3SH$ with ice-acetone cooling. The mixture is stirred, allowed to warm up and finally refluxed overnight. The mixture is cooled, acidified with HOAc and taken to near dryness in vacuum. The residue is dissolved in water and the product extracted into $CHCl_3$. Drying and solvent removal leaves 22 g of crude products. These are chromatographed on 500 g neutral Alumina II. Early fractions (1-2% MeOH in $CHCl_3$) elute isomer A (6,7-trans-5,6,7,8-tetrahydro-7-(methylthio)-1,6-naphthalenediol) mp. 116°–122° from ether. Later fractions (5-10% MeOH in $CHCl_3$) elute isomer B (6,7-trans-5,6,7,8-tetrahydro-6-(methylthio)-1,7-naphthalenediol) mp. 132-134° from ether.

B. 2-[(6-Hydroxy-7-methylthio-5,6,7,8-tetrahydro-1-naphthyl)oxy]-2-methylpropionic acid ethyl ester Following the procedure of Example 1, employing the diol of mp. 116°–112°, the title compound is obtained.

EXAMPLE 38

2-[(7-Hydroxy-6-methylthio-5,6,7,8-tetrahydro-1-naphthyl)oxy]-2-methylpropionic acid ethyl ester Following the procedure of Example 1 employing the diol of Example 38 of mp. 132°–134°, the title compound is obtained.

EXAMPLE 39 trans-2[(6-Hydroxy-7-methoxy-5,6,7,8-tetrahydro-1-naphthyl)oxy]-2-methylpropionic acid ethyl ester A. 6,7-trans-5,6,7,8-Tetrahydro-7(or 6)-methoxy-1,6(or 7)-naphthalenediol A solution of 22 g (0.11 m) of the epoxy acetate of Example 26A in 500 ml MeOH is treated with 0.5 g p-toluene sulfonic acid hydrate and stirred overnight. After removal of most of the solvent, the residual liquid is poured into water and the product extracted into $CHCl_3$. Drying and solvent removal leaves 13.3 g of crude product. This is chromatographed on 300 g neutral alumina II. Early fraction, 5% MeOH in $CHCl_3$ yields isomer A 6,7-trans-5,6,7,8-tetrahydro-7-methoxy-1,6-naphthalenediol, mp. 153°–155° from ether-ethyl acetate; later fractions yield isomer B 6,7-trans-5,6,7,8-tetrahydro-6-methoxy-1,7-naphthalenediol mp. 106°–108° from ether.

B. trans-2[(6-Hydroxy-7-methoxy-5,6,7,8-tetrahydro-1-naphthyl)oxy]-2-methylpropionic acid ethyl ester Following the procedure of Example 1, employing the diol of mp. 153°–155°, the title compound is obtained.

EXAMPLE 40

2[(7-Hydroxy-6-methoxy-5,6,7,8-tetrahydro-1-naphthyl)oxy]-2-methylpropionic acid ethyl ester Following the procedure of Example 1 employing the diol of Example 39 of m.p 106°–108°, the title compound is obtained.

EXAMPLE 41 trans-2-[(6-Amino-7-hydroxy-5,6,7,8-tetrahydro-1(and 4)naphthyl)oxy]-2-methylpropionic acid ethyl ester A. trans-6(and 7) -Amino-5,6,7,8-tetrahydro-1,7(and 6)-naphthalenediol To a solution of 20.4 g (0.1 m) of the epoxy acetate of Example 26A in 200 ml dioxane heated to 40° is added a solution of 6.8 g (0.11 m) of NaN$_3$ in 20 ml H$_2$O dropwise. The mixture is heated under reflux overnight, cooled, filtered and taken to dryness. Strong azide absorption in I. R. is noted. The residue is dissolved in EtOH and hydrogenated over PtO$_2$ at 1–3 atm. H$_2$ in a Paar shaker with repeated flushes with H$_2$ to ensure sufficient exposure to H$_2$. Catalyst is filtered off and washed with warm alcohol. Solvent is removed and the residue is triturated with hexane to induce crystallization mp. 172°- 193° (d) from EtoAc-MeOH.

B. trans-2-[(6-Amino-7-hydroxy-5,6,7,8-tetrahydro-1(and 4)naphthyl)oxy]-2-methylpropionic acid ethyl ester Following the procedure of Example 1, employing the above diol, the title compound is obtained.

EXAMPLE 42 trans-2-[(7-Hydroxy-6-isopropylamino-5,6,7,8-tetrahydro-1(and 4)naphthyl)oxy]-2-methylpropionic acid ethyl ester A. 6,7-trans-5,6,7,8-Tetrahydro-7(and 6)-(isopropylamino)-1,6(and 7)-naphthalenediol A mixture of 10.7 g (0.05 m) of the epoxy acetate of Example 26A and 50 ml of i-propylamine is heated in a bomb at 100° overnight. Removal of excess amine leaves a viscous material that is chromatographed on 500 g of neutral alumina III. 10–20% MeOH in CHCl$_3$ elutes the desired product. The product (a mixture of the above isomers) is crystallized from ether and found to have a mp of 112°–117°. The hydrochloride salt has a mp 207°–210°.

B. trans-2-[(7-Hydroxy-6-ispropylamino-5,6,7,8-tetrahydro-1(and 4)-naphthyl)oxy]-2-methylpropionic acid ethyl ester Following the procedure of Example 1, employing the above diol, the title compound is obtained.

What is claimed is:

1. A compound of the formula:

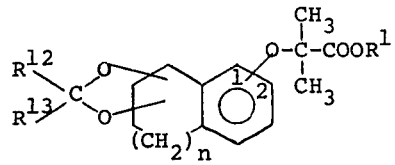

wherein R$^1$ is selected from the group consisting of hydrogen and lower alkyl of 1 to 8 carbons; n is zero, 1 or 2; R$^{12}$ and R$^{13}$ are independently selected from the group consisting of hydrogen and lower alkyl of 1 to 8 carbons; the

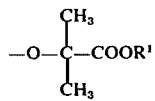

side chain is in either the 1 or 2 position; and the pharmaceutically acceptable salts thereof.

2. The compound of claim 1 wherein the

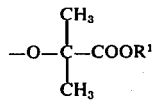

side chain is at the 1-position.

3. The compound of claim 2 wherein n is 1; R$^{12}$ and R$^{13}$ are methyl; and R$^1$ is ethyl.

4. The compound of claim 2 wherein n is 1; R$^{12}$ is hydrogen, R$^{13}$ is n-propyl; and R$^1$ is ethyl.

5. The compound of claim 1 wherein the

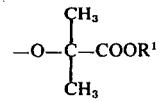

side chain is at the 2-position; n is 1; R$^{12}$ is hydrogen; R$^{13}$ is n-propyl; and R$^1$ is ethyl.

* * * * *

UNITED STATES PATENT AND TRADEMARK OFFICE
CERTIFICATE OF CORRECTION

PATENT NO. : 3,943,149
DATED : March 9, 1976
INVENTOR(S) : Hauck

It is certified that error appears in the above-identified patent and that said Letters Patent are hereby corrected as shown below:

Col. 1, line 25, "droalkyl" should read --droxyalkyl--.

Col. 1, line 50, "formyl" should read --formyl,--.

Col. 2, lines 36-38, "$\overset{M-R^{14}}{\underset{-C-}{\|}}$" should read -- $\overset{N-R^{14}}{\underset{-C-}{\|}}$ --.

Col. 21, line 39, "are" should read --were--.

Col. 23, line 7, "ChCl$_3$" should read -- CHCl$_3$ --.

Col. 25, line 37, "0°c" should read --0°C--.

Col. 27, line 2, a comma should be inserted at the end of the line.

Col. 27, line 44, "alluminum" should read --aluminum--.

Signed and Sealed this twenty-ninth Day of June 1976

[SEAL]

Attest:

RUTH C. MASON
*Attesting Officer*

C. MARSHALL DANN
*Commissioner of Patents and Trademarks*